(12) United States Patent
Sato et al.

(10) Patent No.: US 9,872,603 B2
(45) Date of Patent: Jan. 23, 2018

(54) ENDOSCOPE CONNECTOR AND ENDOSCOPE REPROCESSOR

(71) Applicant: OLYMPUS CORPORATION, Tokyo (JP)

(72) Inventors: Norito Sato, Sagamihara (JP); Masayoshi Aono, Ome (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/202,938

(22) Filed: Jul. 6, 2016

(65) Prior Publication Data

US 2016/0309989 A1  Oct. 27, 2016

Related U.S. Application Data

(63) Continuation of application No. PCT/JP2015/074844, filed on Sep. 1, 2015.

(30) Foreign Application Priority Data

Nov. 25, 2014  (JP) .................................. 2014-238023

(51) Int. Cl.
*A61B 1/12* (2006.01)
*A61B 1/00* (2006.01)
*A61B 1/015* (2006.01)

(52) U.S. Cl.
CPC .......... *A61B 1/00119* (2013.01); *A61B 1/015* (2013.01); *A61B 1/12* (2013.01)

(58) Field of Classification Search
CPC ............ A61B 1/00112; A61B 1/00119; A61B 1/00121; A61B 1/00128
(Continued)

(56) References Cited

U.S. PATENT DOCUMENTS

2005/0065405 A1  3/2005  Hasegawa
2010/0004510 A1  1/2010  Kuroshima

FOREIGN PATENT DOCUMENTS

EP  1502538 A1  2/2005
EP  2 098 185 A1  9/2009
(Continued)

OTHER PUBLICATIONS

International Search Report dated Nov. 17, 2015 issued in PCT/JP2015/074844.
(Continued)

*Primary Examiner* — Matthew J Kasztejna
(74) *Attorney, Agent, or Firm* — Scully, Scott, Murphy & Presser, P.C.

(57) ABSTRACT

A connector functioning as an endoscope connector includes an outer cylinder member, an inner cylinder member, and an urging member. The outer cylinder member includes a channel, an inner circumferential section provided in an inner circumference of the channel, and an inner circumferential section provided further on the outflow port side than the inner circumferential section. The inner cylinder member includes an advancing/retracting section disposed to be capable of advancing and retracting along the channel and having an outer diameter smaller than an outer diameter of the inner circumferential section, an O-shaped ring disposed in an outer circumference of the advancing/retracting section and configured to fill a gap between the advancing/retracting section and the inner circumferential section when the advancing/retracting section is disposed in the inner circumferential section, and a through-path that pierces through the advancing/retracting section along the channel.

9 Claims, 13 Drawing Sheets

(58) Field of Classification Search
USPC .................................. 600/132–133, 158–159
See application file for complete search history.

(56) References Cited

FOREIGN PATENT DOCUMENTS

| JP | H09-078642 A | 3/1997 |
| JP | 08-024813 | * 10/2001 |
| JP | 2001-299697 A | 10/2001 |
| JP | 3718314 B2 | 11/2005 |
| JP | 2010-011977 A | 1/2010 |
| WO | WO 2004/049924 A1 | 6/2004 |
| WO | 2010/045055 A2 | 4/2010 |

OTHER PUBLICATIONS

Extended Supplementary European Search Report dated Oct. 4, 2017 in European Patent Application No. 15 86 3952.6.

* cited by examiner

ENDOSCOPE CONNECTOR AND ENDOSCOPE REPROCESSOR

CROSS REFERENCE TO RELATED APPLICATION

This application is a continuation application of PCT/JP2015/074844 filed on Sep. 1, 2015 and claims benefit of Japanese Application No. 2014-238023 filed in Japan on Nov. 25, 2014, the entire contents of which are incorporated herein by this reference.

BACKGROUND OF THE INVENTION

1. Field of the Invention

The present invention relates to an endoscope connector and an endoscope reprocessor.

2. Description of the Related Art

Endoscopes have been widely used for in-vivo tests and treatments. Since an endoscope is inserted into a body, the endoscope is cleaned after use. An endoscope cleaning/disinfecting apparatus for cleaning the endoscope has also been widely used.

In the cleaning of the endoscope by the endoscope cleaning/disinfecting apparatus, not only a surface of the endoscope but also insides of respective conduits provided on an inside of the endoscope are cleaned. Therefore, respective pipe sleeves communicating with the respective conduits in the endoscope and the endoscope cleaning/disinfecting apparatus (hereinafter simply referred to as cleaning apparatus as well) are connected by a cleaning tube, which is an endoscope connector, a cleaning solution, a disinfecting solution, a rinsing solution, and the like are fed into the respective conduits of the endoscope, whereby the insides of the respective conduits are cleaned and disinfected.

The endoscope connector, which connects the cleaning apparatus and the pipe sleeves of the endoscope, and the cleaning apparatus explained above are disclosed in, for example, Japanese Patent Application Laid-Open Publication No. 2001-299697.

The cleaning apparatus disclosed in Japanese Patent Application Laid-Open Publication No. 2001-299697 includes a flow-rate measuring section that measures a flow rate of fluid delivered to the endoscope connector and includes a configuration that notifies, when a measurement result of the flow rate is outside a range of a set value, a user of the measurement result.

The cleaning apparatus disclosed in Japanese Patent Application Laid-Open Publication No. 2001-299697 measures the flow rate of the fluid delivered to the endoscope connector making use of a phenomenon in which a difference occurs in the flow rate of the fluid delivered from the cleaning apparatus to the endoscope connector when a pipe sleeve coupling section, that is, a connector section of the endoscope connector is correctly attached to the pipe sleeve of the endoscope and when the connector section of the endoscope connector is off the pipe sleeve. The cleaning apparatus compares the flow rate with the set value to thereby determine whether the connector section of the endoscope connector is correctly attached to the pipe sleeve of the endoscope.

In order for the cleaning apparatus explained above to correctly determine that the connector section of the endoscope connector is off the pipe sleeve, the difference in the flow rate is desirably large.

SUMMARY OF THE INVENTION

An endoscope connector according to an aspect of the present invention is a member connected to a pipe sleeve of an endoscope, the endoscope connector including: an outer cylinder member including an inflow port to which a fluid delivering apparatus is connected, an outflow port for feeding out fluid that flows in from the inflow port, a channel that connects the inflow port and the outflow port, and a first inner circumferential section provided on an inner side of the channel; an inner cylinder member including an advancing/retracting section disposed to be capable of advancing and retracting along the channel and having an outer diameter smaller than an outer diameter of the first inner circumferential section, and a through-path that pierces through the advancing/retracting section along the channel; an urging member disposed in the first inner circumferential section and configured to urge the inner cylinder member toward the outflow port; and a watertight section disposed in an outer circumference of the advancing/retracting section or in the first inner circumferential section and configured to fill a gap between the advancing/retracting section and the first inner circumferential section when the advancing/retracting section is disposed in the first inner circumferential section. The fluid introduced from the inflow port when the advancing/retracting section and the first inner circumferential section are arranged side by side in a watertight manner sandwiching the watertight section is fed out passing through the through-path, and the fluid introduced from the inflow port when the watertight section is not sandwiched by the advancing/retracting section and the first inner circumferential section is fed out passing through the through-path and a gap between the inner cylinder member and the outer cylinder member.

An endoscope reprocessor according to another aspect of the present invention includes the endoscope connector of the present invention.

DETAILED DESCRIPTION OF THE PREFERRED EMBODIMENTS

An embodiment of the present invention is explained below with reference to the drawings.

Note that, in respective views used in the following explanation, scales are varied for each of components in order to show the respective components in sizes recognizable on the drawings. The present invention is not limited only to numbers of the components, shapes of the components, ratios of seizes of the components, and relative positional relations among the respective components described in these views.

(Overall Configuration of an Endoscope Cleaning/Disinfecting Apparatus)

Figure 1:
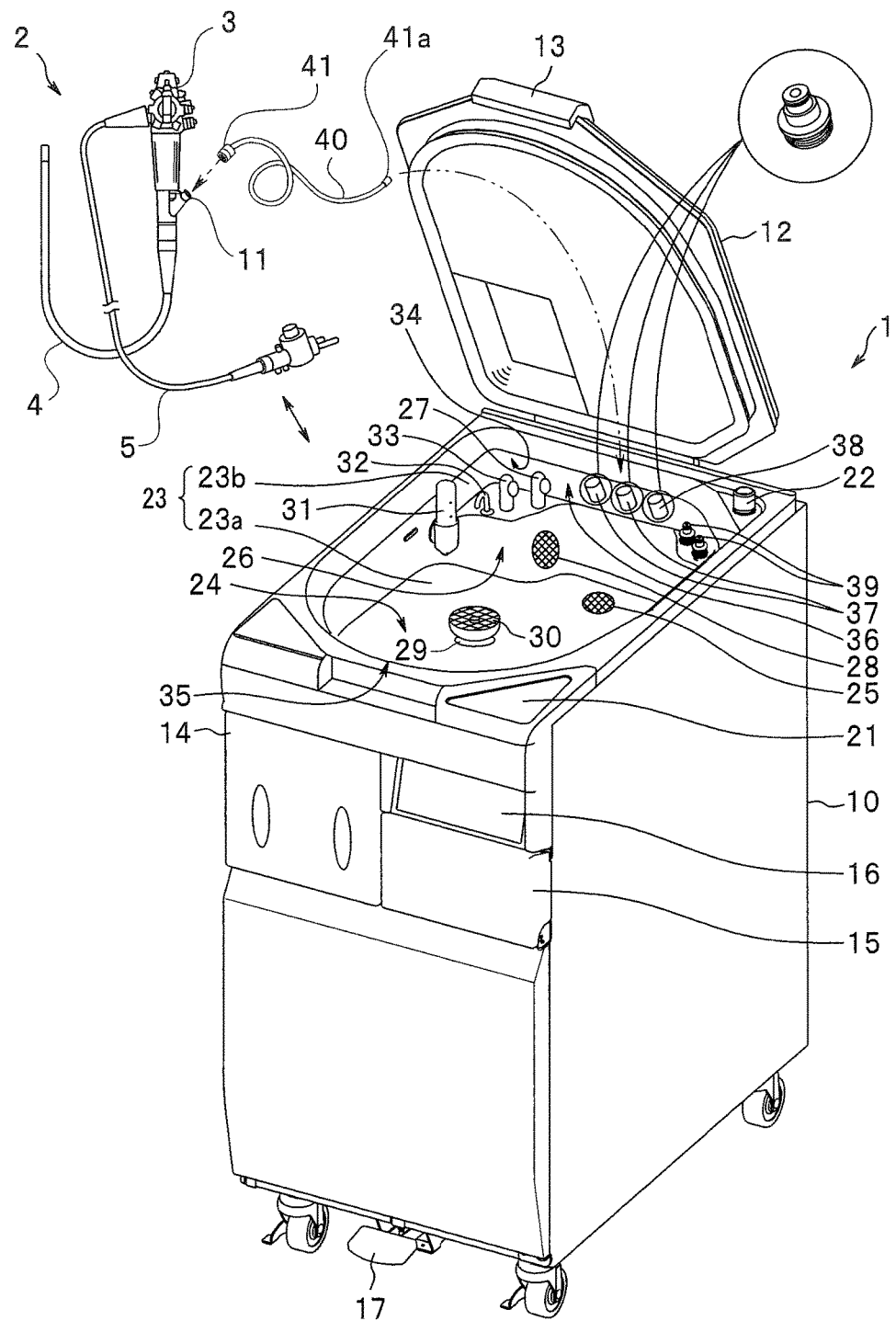
FIG. 1 is a perspective view of an endoscope cleaning/disinfecting apparatus showing a state in which a top cover is opened and an endoscope can be housed in a treatment tank according to an embodiment of the present invention.

FIG. 1 is a perspective view of an endoscope reprocessor showing a state in which a top cover is opened and an endoscope can be housed in a treatment tank.

The endoscope reprocessor is an apparatus that performs reproduction processing of a contaminated endoscope or endoscope accessories. The reproduction processing is not particularly limited and may be any one of a rinse by water, cleaning for removing soil such as organic matters, disinfection for invalidating predetermined microorganisms, sterilization for eliminating or extinguishing all microorganisms, and a combination of the rise, the cleaning, the disinfection, and the sterilization. As an example, an endoscope cleaning/disinfecting apparatus for cleaning and disinfecting an endoscope, which is a type of the endoscope reprocessor, is shown in FIG. 1.

As shown in FIG. 1, the endoscope cleaning/disinfecting apparatus, that is, a cleaning apparatus 1 is a fluid delivering apparatus for cleaning and disinfecting a used endoscope 2. A main part of the endoscope cleaning/disinfecting apparatus 1 is configured by an apparatus main body 10 and a top cover 12, which is a lid body openably and closably connected to an upper part of the apparatus main body 10 via, for example, a not-shown hinge.

The endoscope 2 includes an operation section 3, an elongated insertion section 4 having flexibility extending from the operation section 3, and a universal cable 5 connected to a processor apparatus or the like. An operation knob, operation buttons, and the like are disposed on the operation section 3.

The endoscope cleaning/disinfecting apparatus 1 is configured such that the top cover 12 is fixed to the apparatus main body 10 by a latch 13 in a state in which the top cover 12 is closed to the apparatus main body 10.

On a front surface in the figure (hereinafter referred to as front surface), to which an operator is adjacent, of the apparatus main body 10 and for example, in an upper part of a left half section, a detergent/alcohol tray 14 is disposed to be capable of being drawn out to a front of the apparatus main body 10. On the front surface of the apparatus main body 10 and, for example, in the upper part of the right half section, a cassette tray 15 is disposed to be capable of being drawn out to the front of the apparatus main body 10.

Further, on the front surface of the apparatus main body 10 and in an upper part of the cassette tray 15, a sub-operation panel 16, which displays a cleaning/disinfection time and instruction buttons for heating a disinfecting solution and the like are disposed, is disposed. In a lower part on the front surface in the figure of the apparatus main body 10, a pedal switch 17 for opening the top cover 12, which is closed in an upper part of the apparatus main body 10, to above the apparatus main body 10 according to stepping operation of the operator is disposed.

On an upper surface of the apparatus main body 10, for example, near both ends on the front surface side to which the operator is adjacent, main operation panels 21, on which setting switches such as cleaning and disinfecting operation start switches and cleaning and disinfection mode selection switches of the apparatus main body 10 are disposed, is provided.

On the upper surface of the apparatus main body 10 and on an opposite side of the front surface to which the operator is adjacent, a water-supply-hose connecting section 22, to which a hose connected to a tap is connected, for supplying tap water to the apparatus main body 10 is disposed.

Further, in substantially a center of the upper surface of the apparatus main body 10, a treatment tank 23, in which the endoscope 2 can be housed, is provided. The treatment tank 23 is configured by a tank main body 23a and a terrace section 23b continuously provided around an outer circumferential edge of an endoscope housing port of the tank main body 23a.

When the endoscope 2 after use is cleaned and disinfected, the endoscope 2 can be stored in the tank main body 23a. On a bottom surface 24, which is a surface in a tank of the tank main body 23a, a drain port 25 for draining, from the tank main body 23a, a cleaning solution, water, alcohol, a disinfecting solution, and the like supplied to the tank main body 23a is provided.

In any position on a circumferential side surface 26, which is a surface in the tank of the tank main body 23a, a circulation port 28 for supplying liquid, which is supplied to the tank main body 23a, to the tank main body 23a again is provided. In the case of the present embodiment, examples of the liquid include water, a cleaning solution, alcohol, and a disinfecting solution. However, when the endoscope reprocessor is used as an endoscope sterilizing apparatus, the liquid also includes a sterilization solution.

In the treatment tank 23, a not-shown ultrasound transducer and a not-shown heater are disposed on a rear surface side of the tank main body 23a and a cleaning case 30 is disposed in a conduit disinfecting port 29 disposed substantially in a center of the bottom surface 24 of the tank main body 23a. In any position of the side surface 26 of the tank main body 23a, a level sensor 31 for detecting a level of liquid supplied to the tank main body 23a is provided.

On a surface other than a terrace surface of the terrace section 23b, a detergent nozzle 32 for supplying detergent to be diluted to predetermined concentration and a disinfecting solution nozzle 33 for supplying a diluted and prepared disinfecting solution are disposed. Further, a water supply and circulation nozzle 27 is disposed on a surface of the terrace section 23b parallel to the bottom surface 24 of the tank main body 23a.

On a surface 36 on a side opposed to an operator adjacent position 35 of a terrace surface 34 of a terrace section 23b, a plurality of, that is, two ports 37 for air/water feeding/forceps port, which are fluid supplying sections for supplying fluid to a channel serving as an endoscope conduit provided on an inside of the endoscope 2, a port for forceps raising 38, and a port for water leak detection 39 are disposed.

Connectors 41 and 41a are provided at both ends of the cleaning tube 40. A pipe sleeve 11 communicating with a conduit in the endoscope 2 is provided in the endoscope 2. The connector 41 is an endoscope side connector connected to the pipe sleeve 11 communicating with the conduit in the endoscope 2 and has a substantially cylindrical shape. The connector 41a is an apparatus side connector connected to the ports 37 for water/air feeding/forceps port.

During cleaning of the endoscope 2, liquid such as a cleaning solution supplied through the cleaning tube 40 is supplied into the conduit in the endoscope 2 from the connector 41 through the pipe sleeve 11.

The endoscope cleaning/disinfecting apparatus 1 in the present embodiment includes a flow control function for detecting conduit clogging in the channel of the endoscope 2 during cleaning/disinfection and a flow-rate detecting function for detecting come-off of the connector 41 of the cleaning tube 40 from the pipe sleeve 11. Note that, since specific configurations and action concerning the flow control function and the flow-rate detecting function are publicly known, detailed explanation of the configurations and action is omitted. However, for example, at least a part of a technique disclosed in Japanese Patent Application Laid-Open Publication No. 2014-147643 can be applied.

(Configuration of the Connector 41)

A configuration of a connector 41, which is an endoscope side connector, is explained.

Figure 2:
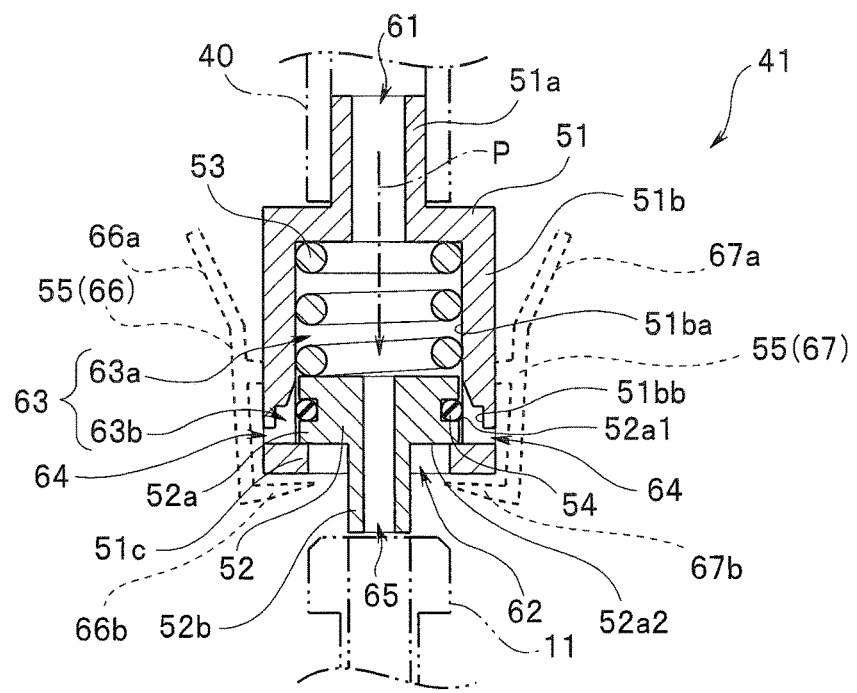
FIG. 2 is a sectional view showing a configuration of a connector 41 according to the embodiment of the present invention.
Figure 3:
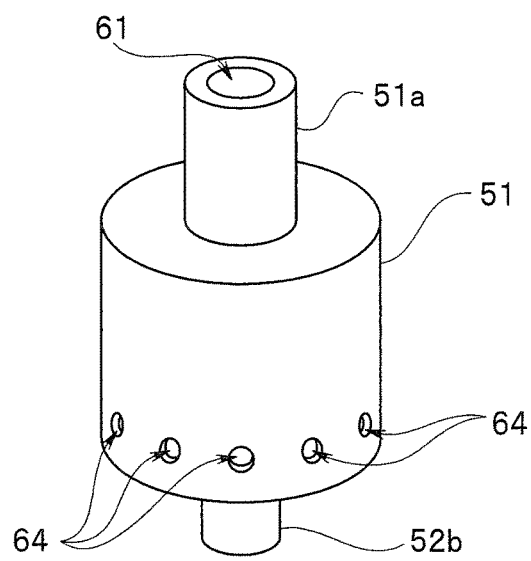
FIG. 3 is a perspective view of the connector 41 according to the embodiment of the present invention.

FIG. 2 is a sectional view showing the configuration of the connector 41. FIG. 2 shows a cross section taken along an axial direction of the substantially cylindrical connector 41. FIG. 3 is a perspective view of the connector 41.

The connector 41 is an endoscope connector including an outer cylinder member 51, an inner cylinder member 52, and an urging member 53. The cleaning tube 40 is connected to the connector 41. The connector 41 is connected to a pipe sleeve of an endoscope.

The outer cylinder member 51 is a cylindrical member including a cleaning-tube connecting section 51a to which the cleaning tube 40 is connected and a housing section 51b, on an inner side of which the urging member 53 and the inner cylinder member 52 are housed. The outer cylinder member 51 may be made of metal or may be made of resin. When the outer cylinder member 51 is made of metal, stainless steel excellent in chemical resistance is desirable.

The cleaning-tube connecting section 51a includes an inflow port 61 connected to the endoscope cleaning/disinfecting apparatus 1, which is the fluid delivering apparatus. Liquid, which is fluid, flows into the outer cylinder member 51 from the inflow port 61. The housing section 51b includes an outflow port 62 from which the liquid, which is the fluid, that flows in from the inflow port 61 flows out. A route connecting the inflow port 61 and the outflow port 62 configures a channel P in which the fluid flows.

In the connector 41, the inflow port 61 side is referred to as proximal end side and the outflow port 62 side is referred to as distal end side. Therefore, the fluid flows from the inflow port 61 on the proximal end side toward the outflow port 62 on the distal end side.

The cleaning-tube connecting section 51a is configured such that a proximal end side portion of the cleaning-tube connecting section 51a is inserted into a distal end portion of the cleaning tube 40, whereby the cleaning tube 40 is fixed to the cleaning-tube connecting section 51a.

The housing section 51b of the outer cylinder member 51 is disposed on the distal end side of the cleaning-tube connecting section 51a. An internal space 63 is formed on an inner side of the housing section 51b. The internal space 63 is formed by a first inner circumferential section 63a and a second inner circumferential section 63b that form two spaces adjacent to each other. The first inner circumferential section 63a of the outer cylinder member 51 is formed on the proximal end side of the internal space 63. The second inner circumferential section 63b is formed on the distal end side of the internal space 63. As shown in FIG. 2, the second inner circumferential section 63b has a columnar shape expanded in diameter with respect to the first inner circumferential section 63a having a columnar shape.

The first inner circumferential section 63a is defined by an inner circumferential surface 51ba on the proximal end side of the housing section 51b. The second inner circumferential section 63b is defined by an inner circumferential surface 51bb formed further on the distal end side than the inner circumferential surface 51ba. The urging member 53 is housed in the first inner circumferential section 63a.

That is, the outer cylinder member 51 includes the inner circumferential section 63a provided in an inner circumference of the channel P and the second inner circumferential section 63b provided further on the outflow port 62 side than the first inner circumferential section 63a in the channel P and having an inner diameter larger than an inner diameter of the first inner circumferential section 63a.

The outer cylinder member 51 includes an inward flange section 51c formed on the distal end side of the housing section 51b. An inner diameter of the inward flange section 51c has a size for enabling the pipe sleeve 11 of the endoscope 2 to pass through the inward flange section 51c. An inner side of the inward flange section 51c forms the outflow port 62.

Further, in a thin portion on the distal end side of the cylindrical housing section 51b, as shown in FIG. 3, a plurality of through-holes 64 piercing through the thin portion to an inner side and an outer side are formed. The plurality of through-holes 64 are disposed along a circumferential direction of the housing section 51b.

The respective through-holes 64 are holes, cross sections of which have a circular shape, opened from the inner circumferential surface 51bb to an outer surface of the housing section 51b. Note that the cross sections of the respective through-holes 64 may have a rectangular shape. Further, only one through-hole 64 may be provided.

The inner cylinder member 52 is disposed to be capable of moving in the internal space 63 of the outer cylinder member 51. That is, the inner cylinder member 52 is disposed to be capable of advancing and retracting along the channel P. The inner cylinder member 52 is made of metal such as stainless steel but may be made of resin.

The inner cylinder member 52 includes an advancing/retracting section 52a that advances and retracts along a channel in the internal space 63 and a pipe sleeve insertion section 52b inserted into the pipe sleeve 11 of the endoscope 2. The inner cylinder member 52 includes, along the channel, a through-path 65 that pierces through the pipe sleeve insertion section 52b from the advancing/retracting section 52a.

An inner diameter of the through-path 65 of the pipe sleeve insertion section 52b disposed on the inner side of the outflow port 62 is smaller than an inner diameter of the inflow port 61. In other words, an opening area of the through-path 65 is smaller than an opening area of the inflow port 61.

The advancing/retracting section 52a has a columnar shape. An outer diameter of the advancing/retracting section 52a is smaller than an inner diameter of the first inner circumferential section 63a. The advancing/retracting section 52a includes a groove section 52a1 formed along a circumferential direction. An O-shaped ring 54 is attached to the groove section 52a1. An outer diameter of the O-shaped ring 54 attached to the advancing/retracting section 52a is slightly larger than the inner diameter of the first inner circumferential section 63a.

When the O-shaped ring 54 attached to the advancing/retracting section 52a is present inside the first inner circumferential section 63a, the O-shaped ring 54 configures a watertight section that fills a gap between the advancing/retracting section 52a and the inner circumferential surface 51ba. The O-shaped ring 54 is an elastic member made of silicone, fluorocarbon rubber, or the like. When the O-shaped ring 54 attached to the advancing/retracting section 52a is present inside the second inner circumferential section 63b, the O-shaped ring 54 has an outer diameter that causes the gap between the advancing/retracting section 52a and the inner circumferential surface 51ba.

That is, the inner cylinder member 52 includes the advancing/retracting section 52a disposed to be capable of advancing and retracting along the channel P and having the outer diameter smaller than the outer diameter of the second inner circumferential section 63b, the O-shaped ring 54, which is the watertight section disposed in an outer circumference of the advancing/retracting section 52a to fill a gap between the advancing/retracting section 52a and an inner circumferential surface of the first inner circumferential section 63a when the advancing/retracting section 52a is disposed in the first inner circumferential section 63a, and the through-path 65 that pierces through the advancing/retracting section 52a along the channel P.

Shapes in cross sections orthogonal to the channel P of the outer cylinder member 51 and the inner cylinder member 52 are circular shapes. However, the shapes may be other shapes such as a square shape, a rectangular shape, and a polygonal shape.

The urging member 53 is provided inside the first inner circumferential section 63a in a compressed state to urge the inner cylinder member 52 to the distal end side. That is, the urging member 53 is disposed in the first inner circumferential section 63a and urges the inner cylinder member 52 toward the outflow port 62. In the present embodiment, a coils spring is used as the urging member 53. However, the present invention is not limited to this. For example, a leaf spring or an elastic member may be used as the urging member 53.

The inner cylinder member 52 is urged to the distal end side of the connector 41 by the urging member 53. The outer cylinder member 51 is configured such that, when the connector 41 is not attached to the pipe sleeve 11, a distal end face 52a2 of the advancing/retracting section 52a is in contact with the inward flange section 51c of the outer cylinder member 51 and the advancing/retracting section 52a is not pushed out to the distal end side of the outer cylinder member 51.

That is, the O-shaped ring 54 is provided in the inner cylinder member 52 such that, when the connector 41 is not attached to the pipe sleeve 11, the O-shaped ring 54 is located inside the second inner circumferential section 63b and causes a gap between the advancing/retracting section 52a and the inner circumferential surface 51bb and, when the connector 41 is correctly attached to the pipe sleeve 11, the O-shaped ring 54 is located inside the first inner circumferential section 63a and does not cause the gap between the advancing/retracting section 52a and the inner circumferential surface 51ba.

Further, the connector 41 includes a fixing section 55 for fixing the connector 41 when the connector 41 is connected to the pipe sleeve 11.

The fixing section 55 includes two holding members 66 and 67 having elasticity. Centers of the holding members 66 and 67 are fixed to an outer circumferential section of the outer cylinder member 51. In the holding members 66 and 67, knob sections 66a and 67a are respectively formed on the proximal end side and hook sections 66b and 67b are respectively formed on the distal end side.

When the knob sections 66a and 67a are pinched, the holding members 66 and 67 are capable of moving with the centers as fulcrums. The fixing section 55 is configured such that, when the knob sections 66a and 67a are pinched, the hook sections 66b and 67b on the distal end side separate from each other and, when the pinching of the knob sections 66a and 67a is stopped, the hook sections 66b and 67b on the distal end side approach.

When the connector 41 is connected to the pipe sleeve 11, by locking hook sections 61a and 62b to an outward flange section 11a of the pipe sleeve 11, it is possible to fix the connector 41 when the connector 41 is connected to the pipe sleeve 11.

Therefore, the hook sections 66b and 67b of the fixing section 55 provided in the outer cylinder member 51 configure an engaging section that engages with the pipe sleeve 11 of the endoscope 2.

(Action)

Action of the connector 41 explained above is explained.

First, action at the time when the connector 41 is correctly fixed to the pipe sleeve 11 is explained.

Figure 4:
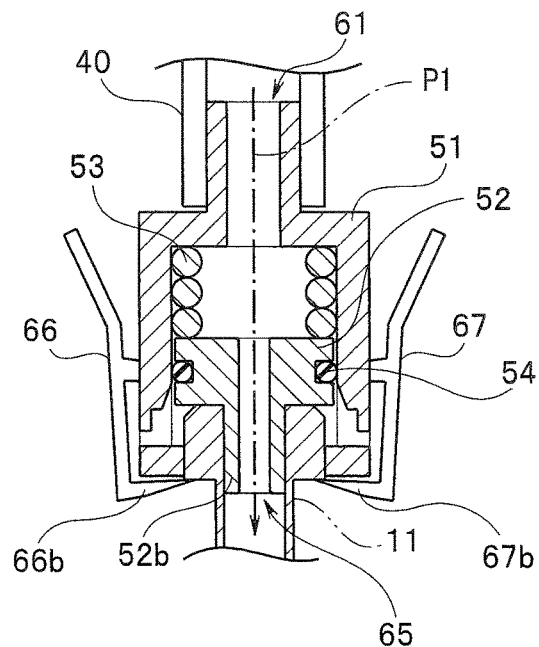
FIG. 4 is a sectional view showing a configuration of the connector 41 at the time when the connector 41 is correctly fixed to a pipe sleeve 11 according to the embodiment of the present invention.

FIG. 4 is a sectional view showing a configuration of the connector 41 at the time when the connector 41 is correctly fixed to the pipe sleeve 11.

When a user inserts the pipe sleeve 11 of the endoscope 2 into the inner side of the inward flange section 51c of the outer cylinder member 51 and the connector 41 is pressed against the pipe sleeve 11, the urging member 53 is compressed and the advancing/retracting section 52a moves to the first inner circumferential section 63a of the internal space 63.

The hook sections 66b and 67b engage with a step section of the pipe sleeve 11, whereby the connector 41 is fixed to the pipe sleeve 11.

As shown in FIG. 4, when the connector 41 is correctly fixed to the pipe sleeve 11, a cleaning solution for cleaning an inside of a conduit connected to the pipe sleeve 11 of the endoscope 2, a disinfecting solution for disinfecting the inside of the conduit connected to the pipe sleeve 11 of the endoscope 2, or a rinsing solution for rinsing the inside of the conduit connected to the pipe sleeve 11 of the endoscope 2 flows into the connector 41 from the cleaning apparatus 1 via the cleaning tube 40. Liquid such as the cleaning solution supplied through the cleaning tube 40 flows into the first inner circumferential section 63a from the inflow port 61 of the connector 41.

The O-shaped ring 54 prevents the liquid from flowing into the second inner circumferential section 63b from the gap between the advancing/retracting section 52a and the inner circumferential surface 51ba. Therefore, the liquid is supplied into the pipe sleeve 11 through the through-path 65 formed in the inner cylinder member 52 as indicated by an alternate long and short dash line P1.

Action at the time when the connector 41 is not correctly fixed to the pipe sleeve 11 and is off the pipe sleeve 11 is explained.

Figure 5:
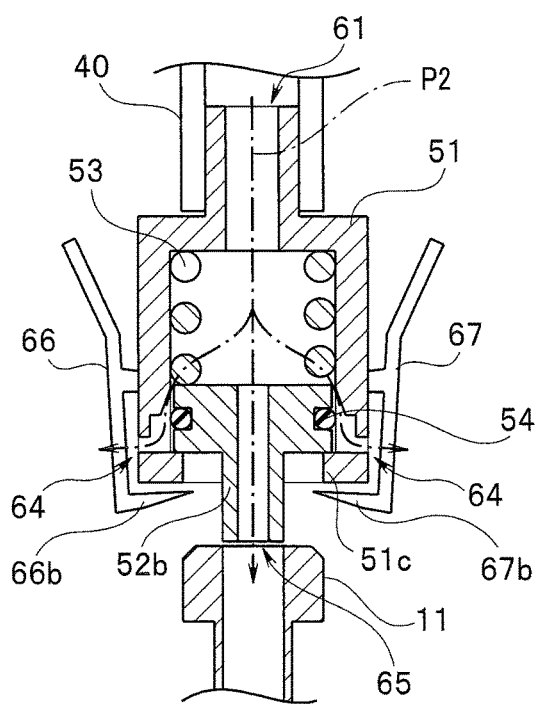
FIG. 5 is a sectional view showing a configuration of the connector 41 at the time when the connector 41 is not correctly fixed to the pipe sleeve 11 and is off the pipe sleeve 11 according to the embodiment of the present invention.

FIG. 5 is a sectional view showing a configuration of the connector 41 at the time when the pipe sleeve 11 is not correctly fixed to the connector 41 and is off the connector 41.

When the connector 41 at the distal end of the cleaning tube 40 is correctly fixed to the pipe sleeve 11 and thereafter comes off the pipe sleeve 11 or the connector 41 is off without being correctly fixed to the pipe sleeve 11, the advancing/retracting section 52a is pushed by the urging member 53 to come into contact with the inward flange section 51c.

In this state, the O-shaped ring 54 is not in contact with the inner circumferential surface 51bb and a gap is formed between the advancing/retracting section 52a and the inner circumferential surface 51bb. Therefore, the liquid that flows into an inside of the first inner circumferential section 63a from the inflow port 61 of the connector 41 flows into the second inner circumferential section 63b from the gap. Further, as indicated by an alternate long and short dash line P2, the liquid flows out to an outside of the connector 41 from the plurality of through-holes 64 as well.

At this point, the liquid flows out from the through-path 65 of the inner cylinder member 52. However, in addition, the liquid flows out from the plurality of through-holes 64 as well. Therefore, a flow rate of the liquid supplied through cleaning tube 40 increases.

That is, the fluid introduced from the inflow port 61 when the advancing/retracting section 52a and the first inner circumferential section 63a are arranged side by side in a watertight manner sandwiching the O-shaped ring 54, which is the watertight section, is fed out passing through the through-path 65. The fluid introduced from the inflow port 61 at the time when the O-shaped ring 54 is not sandwiched by the advancing/retracting section 52a and the first inner circumferential section 63a is fed out passing through the through-path 65 and the gap between the inner cylinder member 52 and the outer cylinder member 51.

The liquid is supplied from the cleaning apparatus 1, which is the liquid delivering apparatus, to the cleaning tube 40 during cleaning. When a flow rate of the liquid flowing inside the cleaning tube 40 when the connector 41 is correctly fixed to the pipe sleeve 11 is represented as Qa and a flow rate of the liquid flowing inside the cleaning tube 40 when the connector 41 is off the pipe sleeve 11 is represented as Qb, Qb>Qa. A difference d between the flow rates Qa and Qb (=Qb−Qa) can be detected by a flow meter (not shown in the figure) provided inside the cleaning apparatus 1.

For example, opening areas of respective opening sections of the plurality of through-holes 64 are designed and the respective opening sections are formed such that the difference d detected by the flow meter provided in the cleaning apparatus 1 is equal to or larger than 0.005 L/Min (i.e., 5 cc per minute).

Therefore, when the connector 41 is not correctly fixed to the pipe sleeve 11 and is off the pipe sleeve 11, the liquid is fed out from the plurality of through-holes 64 as well. Therefore, a change in a flow rate of the liquid flowing inside the cleaning tube 40 can be detected by the flow meter inside the cleaning apparatus 1.

Note that, in the embodiment explained above, the cleaning tube 40 is detachably attachable to the endoscope cleaning/disinfecting apparatus 1. However, the cleaning tube 40 including the connector 41 at one end may be un-detachably attached to the endoscope cleaning/disinfecting apparatus 1.

Therefore, according to the embodiment explained above, it is possible to provide an endoscope connector that can clarify a flow rate difference of fluid between a time when the connector 41, which is the endoscope connector, is correctly connected to the pipe sleeve 11 of the endoscope 2 and a time when the connector 41 comes off the pipe sleeve 11 and an endoscope cleaning/disinfecting apparatus including such an endoscope connector.

Modifications of the embodiment explained above are explained.

Note that, in the respective modifications explained below, components same as the components in the embodiment explained above are denoted by the same reference numerals and signs and explanation of the components is omitted.

(Modification 1)

In the connector 41 in the embodiment explained above, the cleaning-tube connecting section 51a, to which the cleaning tube 40 is connected, is provided at a proximal end portion of the outer cylinder member 51. However, in a modification 1, a cleaning-tube connecting section is provided in a side surface portion of an outer cylinder member.

Figure 6:
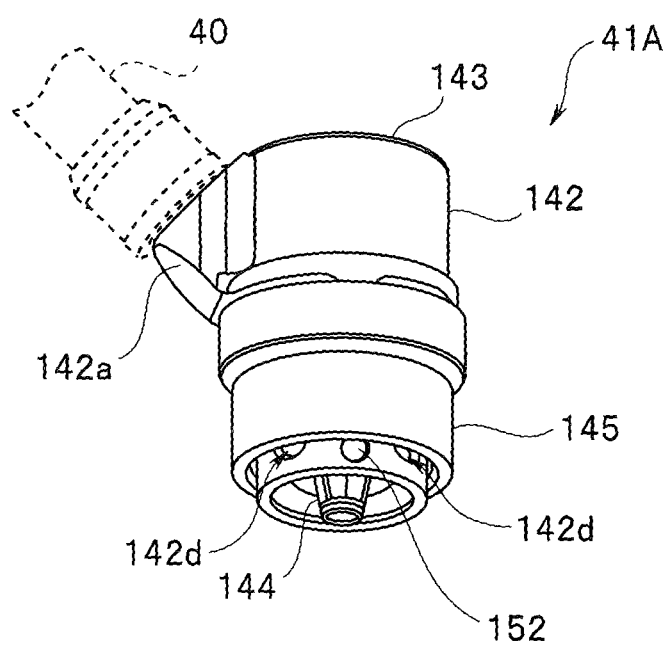
FIG. 6 is a front view of a connector 41A in a modification 1 of the embodiment of the present invention.
Figure 7:
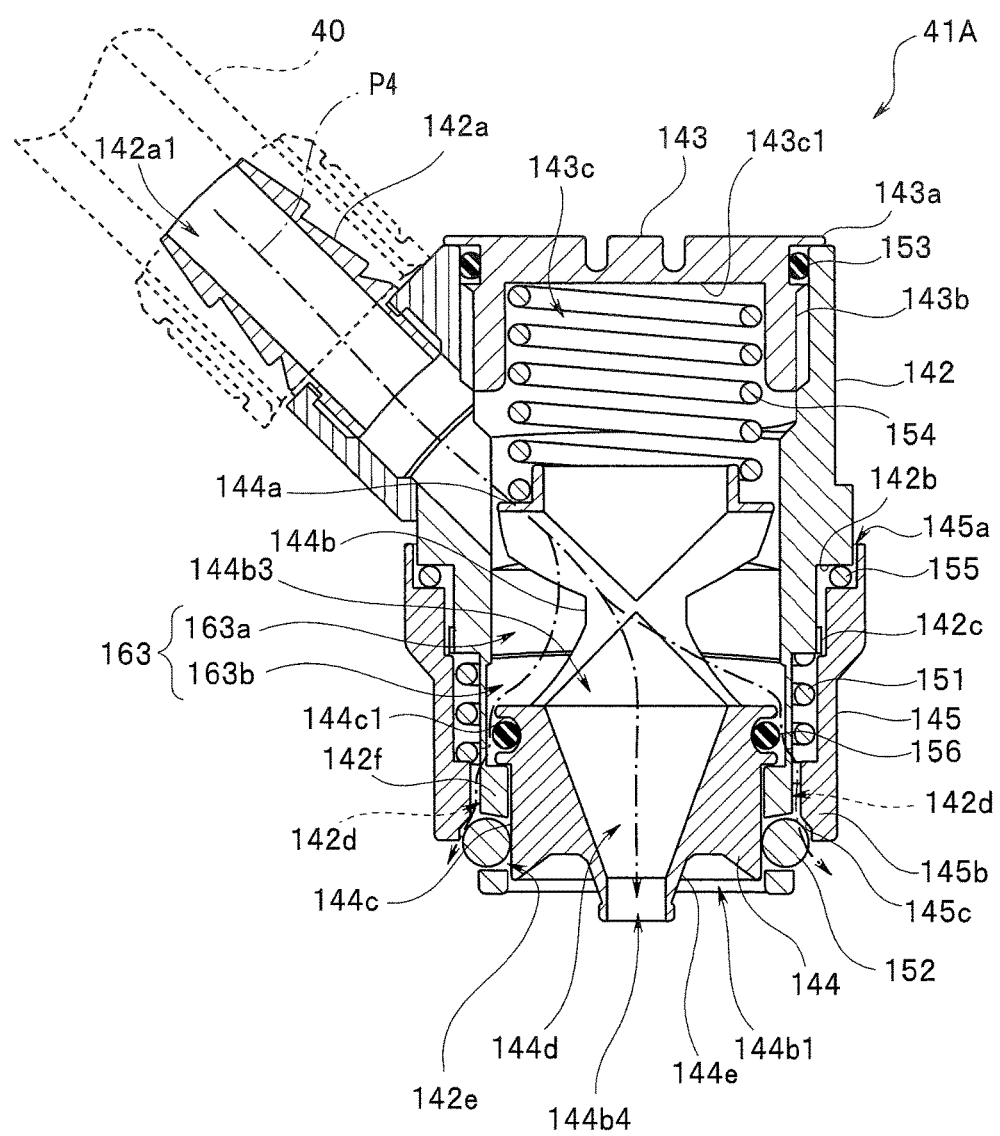
FIG. 7 is a sectional view of the connector 41A taken along a channel of the connector 41A according to the modification 1 of the embodiment of the present invention.
Figure 8:
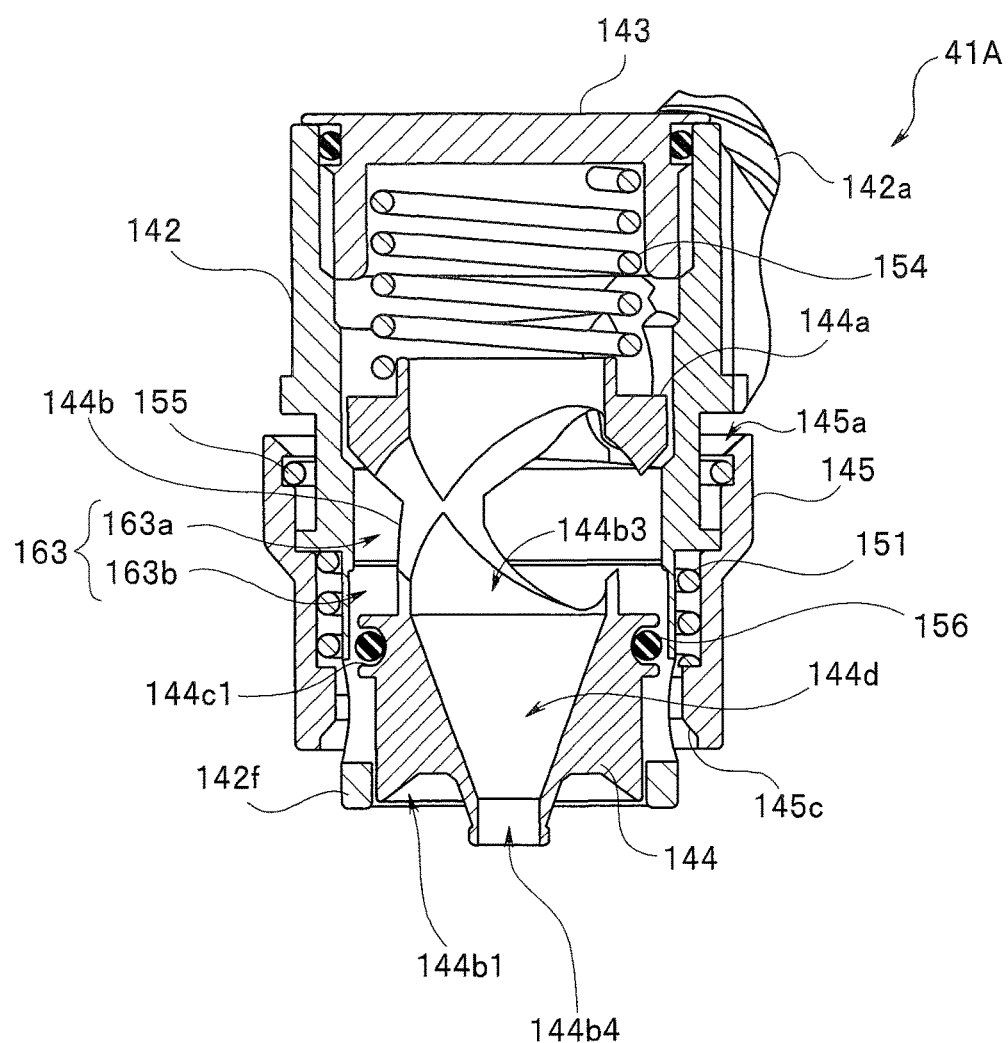
FIG. 8 is a sectional view of the connector 41A taken along the channel of the connector 41A and is a sectional view on a surface different from FIG. 7 according to the modification 1 of the embodiment of the present invention.
Figure 9:
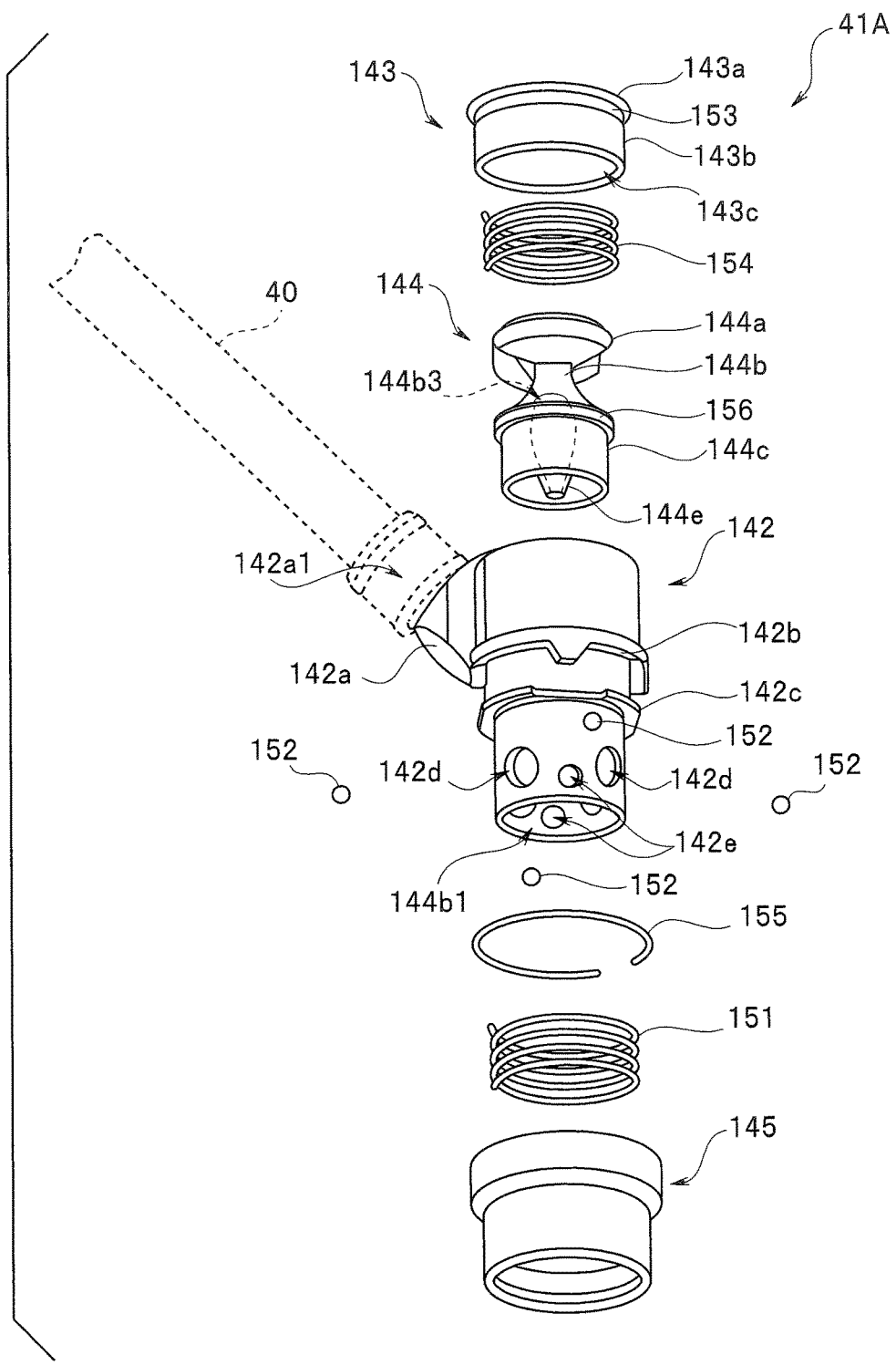
FIG. 9 is an exploded view of the connector 41A according to the modification 1 of the embodiment of the present invention.

FIG. 6 is a front view of a connector 41A in the modification 1. FIG. 7 is a sectional view of the connector 41A taken along a channel of the connector 41A. FIG. 8 is a sectional view of the connector 41A taken along the channel of the connector 41A and a sectional view in a surface different from FIG. 7. FIG. 9 is an exploded view of the connector 41A.

The connector 41A, which is an endoscope connector, includes a main body 142, a lid member 143, a pipe sleeve pressing member 144, and a cover member 145.

The main body 142 is a cylindrical member made of metal or resin and includes a tube connecting section 142a projecting obliquely upward from a side surface of an upper part. The tube connecting section 142a includes a step section on an outer circumferential surface. The cleaning tube 40 made of resin is externally inserted over and connected to the tube connecting section 142a. The tube connecting section 142a includes an inflow port 142a1 to which a fluid delivering apparatus is connected. The inflow port 142a1 communicates with a distal end side opening 144b4 explained below via an opening section 144b3 of the pipe sleeve pressing member 144 explained below. In other words, the connector 41A can introduce fluid, which is supplied from a fluid supply source, from the inflow port 142a1 and discharge the fluid from the distal end side opening 144b4. The inflow port 142a1 configures an inflow port into which liquid delivered from the endoscope reprocessor 1 flows.

A step section 142b is formed along a circumferential direction in an outer circumferential section in a center of the main body 142. A circumferential protrusion section 142c formed along the circumferential direction is provided below the step section 142b. As explained below, one end of a spring 151 is in contact with the protrusion section 142c. A plurality of (four) holes 142d are provided below the protrusion section 142c of the main body 142.

Further, a plurality of (four) holes 142e are formed in the circumferential direction below the main body 142. Inner circumferential surfaces of the respective holes 142e are inclined surfaces reduced in inner diameter from an outer side toward an inner side. As explained below, metal balls 152 are fit in the respective holes 142e from an outer side. The respective balls 152 are caught by taper surfaces of the holes 142e and do not come off to an inner side of the main body 142. The respective holes 142d and the holes 142e are opening sections that cause an inner side and an outer side of the thin portion of the main body 142 of the cylindrical member to communicate each other.

The main body 142 is a member corresponding to the outer cylinder member 51 explained above. An internal space 163 is formed on the inner side of the main body 142. The internal space 163 is formed by two inner circumferential sections adjacent to each other, that is, a first inner circumferential section 163a and a second inner circumferential section 163b. The first inner circumferential section 163a of the main body 142 is formed on the proximal end side of the internal space 163, which is a side into which the liquid flows. The second inner circumferential section 163b is formed on the distal end side of the internal space 163, which is a side from which the liquid flows out. As shown in FIG. 7 and FIG. 8, the second inner circumferential section 163b has a columnar shape expanded in diameter with respect to the first inner circumferential section 163a having a columnar shape. A spring 154 functioning as an urging member is housed in an upper part of the first inner circumferential section 163a.

The main body 142 includes an inward flange section 142f in a lower part. An inner diameter of the inward flange section 142f has a size for enabling the pipe sleeve 11 of the endoscope 2 to pass through the inward flange section 142f. An inner side of the inward flange section 142f forms an outflow port 144b1. A route connecting the inflow port 142a1 and the outflow port 144b1 configures a channel in which the fluid flows.

The lid member 143 made of resin is attached to an upper part of the main body 142. The lid member 143 includes a ring-like projecting section 143a. An extending section 143b extending downward is provided in a lower part of the lid member 143. An O-shaped ring 153 is attached to the extending section 143b. The O-shaped ring 153 is an elastic member made of silicone, fluorocarbon rubber, or the like. When the lid member 143 is attached to an upper part of the main body 142, the O-shaped ring 153 seals the inside of the main body 142.

The extending section 143b includes a recessed section 143c opened to a lower side. The spring 154 is provided inside the recessed section 143c. An upper end of the spring 154 is in contact with a bottom surface 143c1 of the recessed section 143c. A lower end of the spring 154 is in contact with an upper part of the pipe sleeve pressing member 144 explained below. The spring 154 is provided between the lid member 143 and the pipe sleeve pressing member 144 in a compressed state.

The pipe sleeve pressing member 144 is a member corresponding to the inner cylinder member 52 explained above and is made of metal such as stainless steel. The pipe sleeve pressing member 144 has a cylindrical shape. A configuration of the pipe sleeve pressing member 144, which is an endoscope connector, is explained below.

The cover member 145 is externally inserted over and attached to a lower part of the main body 142. The cover member 145 is made of metal such as stainless steel and has a cylindrical shape. A circumferential step section 145a formed along the circumferential direction is formed in an upper part of an inner circumferential surface of the cover member 145. A C-shaped ring 155 made of metal such as stainless steel is fit inside the step section 145a such that the C-shaped ring 155 made of metal such as stainless steel is compressed in an inner diameter direction.

The C-shaped ring 155 fit in the step section 145a bumps against the step section 142b of the main body 142 and restricts the cover member 145 from moving to above the main body 142.

The cover member 145 includes an inward flange section 145b in a lower part. The spring 151 is disposed inside the cover member 145. A lower end portion of the spring 151 is in contact with the inward flange section 145b. An upper end portion of the spring 151 is in contact with the protrusion section 142c of the main body 142. The spring 151 is disposed between the inward flange section 145b and the protrusion section 142c. A taper section 145c is formed in a lower part of the inner circumferential surface of the cover member 145.

The pipe sleeve pressing member 144, which is an endoscope connector, is disposed inside the main body 142 and configures an advancing/retracting section that advances and retracts inside the main body 142.

A step section, with which a lower part of the spring 154 is in contact, is formed in an upper part 144a of the pipe sleeve pressing member 144. A cylindrical section 144c is formed in a lower part of the pipe sleeve pressing member 144. A constricted section 144b is formed in a center of the pipe sleeve pressing member 144. As shown in FIG. 8, the constricted section 144b, which connects the upper part 144a and the cylindrical section 144c, is formed to deviate from an axial center of the main body 142 having a cylindrical shape. An opening section 144b3 is formed below the constricted section 144b.

Further, a lower surface of the cylindrical section 144c of the pipe sleeve pressing member 144 includes a throttle section 144e including a distal end side opening 144b4. The throttle section 144e includes a portion tapered downward. In this modification, the throttle section 144e has a conical shape. The cylindrical section 144c includes a through-path 144*d* that communicates with the distal end side opening 144*b*4 from the opening section 144*b*3.

As explained below, the distal end side opening 144*b*4 of the through-path 144*d* is an opening opened on an inside of the pipe sleeve 11 of the endoscope. Therefore, the opening section 144*b*3 is an opening that communicates with the distal end side opening 144*b*4 and into which the fluid from the fluid supply source flows.

An inner diameter of the distal end side opening 144*b*4 of the throttle section 144*e* disposed on the inner side of the outflow port 144*b*1 is smaller than an inner diameter of the inflow port 142*a*1. In other words, an opening area of the distal end side opening 144*b*4 is smaller than an opening area of the inflow port 142*a*1.

An upper part of the cylindrical section 144*c* of the pipe sleeve pressing member 144 has an outer diameter larger than the inner diameter of the inward flange section 142*f*. Therefore, the upper part of the cylindrical section 144*c* is in contact with the inward flange section 142*f*. The pipe sleeve pressing member 144 is configured not to come off to a lower side (i.e., the distal end side) of the main body 142.

On an outer circumferential surface of the upper part of the cylindrical section 144*c* of the pipe sleeve pressing member 144, a groove along the circumferential direction, that is, an outer circumferential groove 144*c*1 is formed. The O-shaped ring 156 is attached to the outer circumferential groove 144*c*1. When the O-shaped ring 156 is disposed in the first inner circumferential section 163*a*, the O-shaped ring 156 configures a watertight section that fills a gap between the pipe sleeve pressing member 144 and an inner circumferential surface of the first inner circumferential section 163*a*.

The spring 154 is disposed in the step section of the upper part 144*a* of the pipe sleeve pressing member 144. When the lid member 143 is fixed to an upper part of the main body 142 by an adhesive, an upper part of the spring 154 enters inside the recessed section 143*c* of the extending section 143*b* of the lid member 143. A lower part of the spring 154 comes into contact with the step section of the pipe sleeve pressing member 144. The spring 154 is disposed between the bottom surface 143*c*1 of the recessed section 143*c* and the step section of the upper part 144*a* in a compressed state.

Therefore, the pipe sleeve pressing member 144 is urged downward with respect to the lid member 143 by an elastic force of the extending spring 154.

Therefore, in the main body 142, which is the main body member, the pipe sleeve pressing member 144 is urged to the throttle section 144*e* side by the spring 154, which is the elastic member.

(Action)

Action at the time when the connector 41A explained above is attached to the pipe sleeve 11 of the endoscope 2 is explained.

Figure 10:
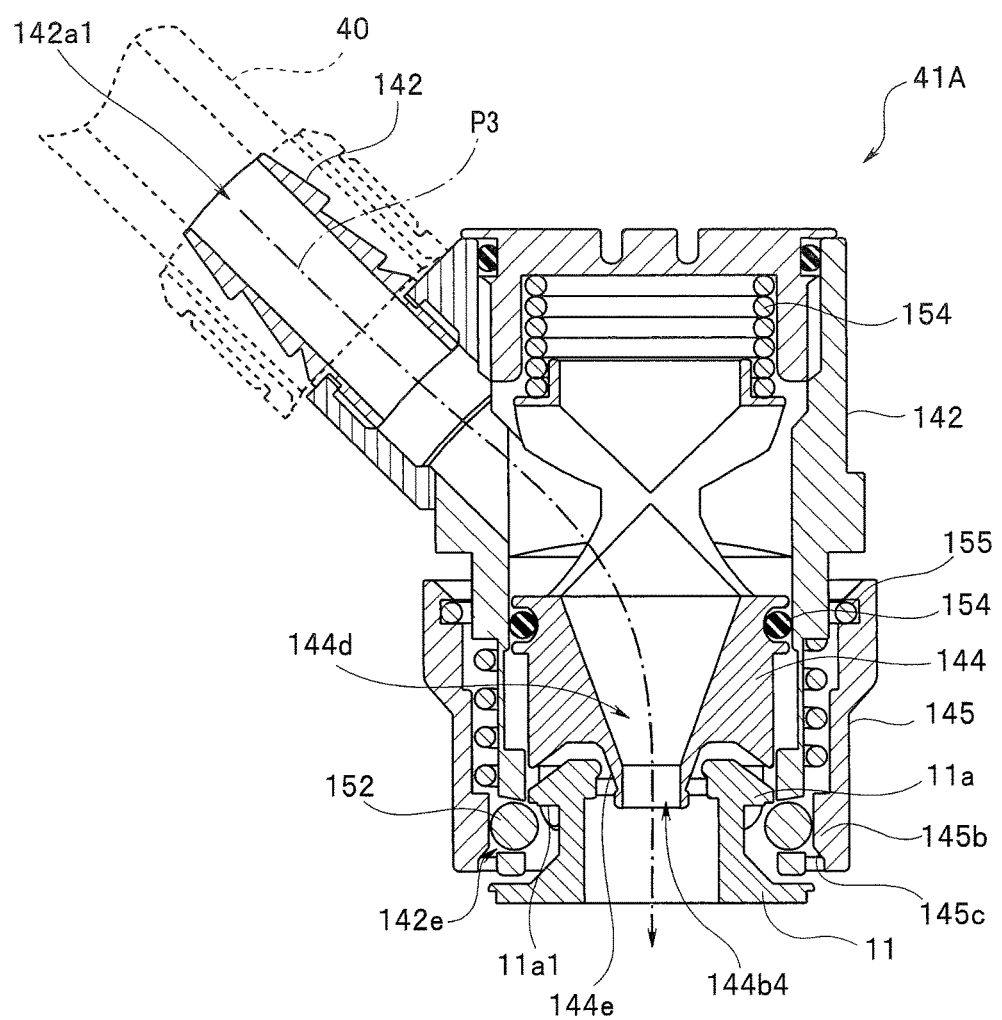
FIG. 10 is a sectional view showing a state in which the connector 41A is attached to the pipe sleeve 11 according to the modification 1 of the embodiment of the present invention.

FIG. 10 is a sectional view showing a state in which the connector 41A is attached to the pipe sleeve 11.

When the connector 41A is correctly attached to the pipe sleeve 11, the throttle section 144*e* of the pipe sleeve pressing member 144 is disposed to be located on an inside in depth from an opening section of the pipe sleeve 11 of the endoscope 2.

At this point, the spring 154 is compressed. In a state in which the spring 154 is compressed, the four balls 152 can enter a lower surface 11*a*1 side of the outward flange section 11*a* of the pipe sleeve 11. Then, when the cover member 145 is pressed against the endoscope 2 side, the inward flange section 145*b* of the cover member 145 pushes the respective balls 152 in an inner diameter direction of the main body 142.

Therefore, a part of the respective balls 152 projects from inner sides of the holes 142*e* and bumps against an outer circumferential edge on a lower side of the outward flange section 11*a* of the pipe sleeve 11. The connector 41A does not come off the pipe sleeve 11.

That is, the cover member 145 covering the main body 142 includes a fixing mechanism for fixing the pipe sleeve pressing member 144 to the pipe sleeve 11 when pipe sleeve pressing member 144 is attached to the pipe sleeve 11 of the endoscope 2. The four balls 152 include an engaging section that engages with the pipe sleeve 11 of the endoscope 2.

Figure 11:
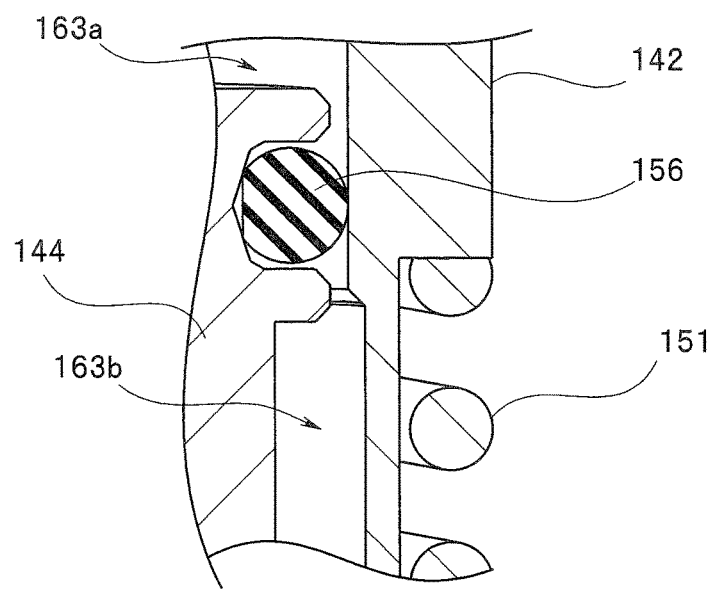
FIG. 11 is a partial sectional view showing a positional relation between an O-shaped ring 156 and an inner circumferential surface of a main body 142 at the time when the connector 41 is correctly fixed to the pipe sleeve 11 according to the modification 1 of the embodiment of the present invention.

FIG. 11 is a partial sectional view showing a positional relation between the O-shaped ring 156 and the inner circumferential surface of the main body 142 at the time when the connector 41A is correctly fixed to the pipe sleeve 11.

When the connector 41A is correctly fixed to the pipe sleeve 11, as shown in FIG. 11, the O-shaped ring 156 prevents the liquid from flowing into an inner side of the inner circumferential section 163*b* from a gap between the pipe sleeve pressing member 144, which is the advancing/retracting section, and the inner circumferential surface of the main body 142. Therefore, as indicated by an alternate long and short dash line P3 in FIG. 10, the liquid that flows in from the inflow port 142*a*1 enters the through-path 144*d* from the opening section 144*b*3 of the pipe sleeve pressing member 144 and is supplied into the pipe sleeve 11 from the distal end side opening 144*b*4.

Figure 12:
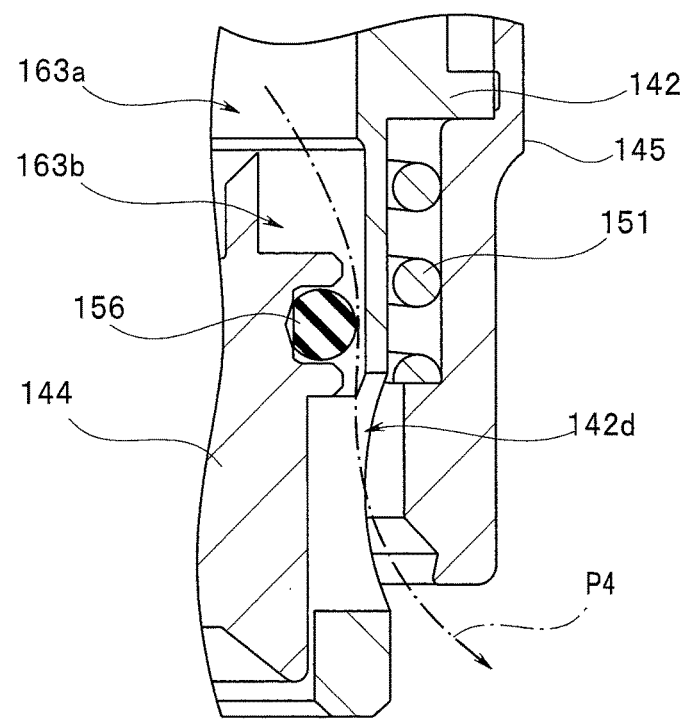
FIG. 12 is a partial sectional view showing a positional relation between the O-shaped ring 156 and the inner circumferential surface of the main body 142 at the time when the connector 41 is not correctly fixed to the pipe sleeve 11 according to the modification 1 of the embodiment of the present invention.

FIG. 12 is a partial sectional view showing a positional relation between the O-shaped ring 156 and the inner circumferential surface of the main body 142 at the time when the connector 41A is not correctly fixed to the pipe sleeve 11. When the connector 41A is not correctly attached to the pipe sleeve 11 and is off from the pipe sleeve 11, as shown in FIG. 12, even if the O-shaped ring 156 is present, the liquid flows into the inner side of the inner circumferential section 163*b* from the gap between the pipe sleeve pressing member 144, which is the advancing/retracting section, and the inner circumferential surface of the main body 142. Therefore, as indicated by an alternate long and short dash line P4 in FIG. 7 and FIG. 12, the liquid that flows in from the inflow port 142*a*1 enters the through-path 144*d* from the opening section 144*b*3 of the pipe sleeve pressing member 144 and is discharged from the distal end side opening 144*b*4. At the same time, the liquid passes through the gap between the pipe sleeve pressing member 144 and the inner circumferential surface of the main body 142 and flows out from the plurality of (four) holes 142*d* of the main body 142.

In this modification 1, as in the embodiment, a size of the gap between the pipe sleeve pressing member 144 and the inner circumferential surface of the main body 142 is set such that a difference between the flow rate Qa of the liquid flowing inside the cleaning tube 40 when the connector 41A is correctly fixed to the pipe sleeve 11 and the flow rate Qb of the liquid flowing inside the cleaning tube 41A when the connector 41 is off the pipe sleeve 11 is detected by the flow meter provided in the cleaning apparatus 1 as, for example, equal to or larger than 0.005 L/Min. Therefore, when the connector 41A is not correctly fixed to the pipe sleeve 11 and is off the pipe sleeve 11, since the liquid is fed out from the plurality of holes 142*d*, which are the through-holes, as well, a change in the flow rate of the liquid flowing inside the cleaning tube 40 can be detected by the flow meter inside the cleaning apparatus 1.

(Modification 2)

In the connector 41 in the embodiment explained above, when the connector 41 is not correctly fixed to the pipe sleeve 11 and is off the pipe sleeve 11, the liquid passed through the gap between the advancing/retracting section 52*a* and the inner circumferential surface 51*ba* flows out from the plurality of through-holes 64 provided on the side surface of the outer cylinder member 51. However, in a connector 41B in a modification 2, the liquid passed through the gap between the advancing/retracting section 52*a* and the inner circumferential surface 51*ba* flows out from the outflow port 62 of the outer cylinder member 51.

Figure 13:
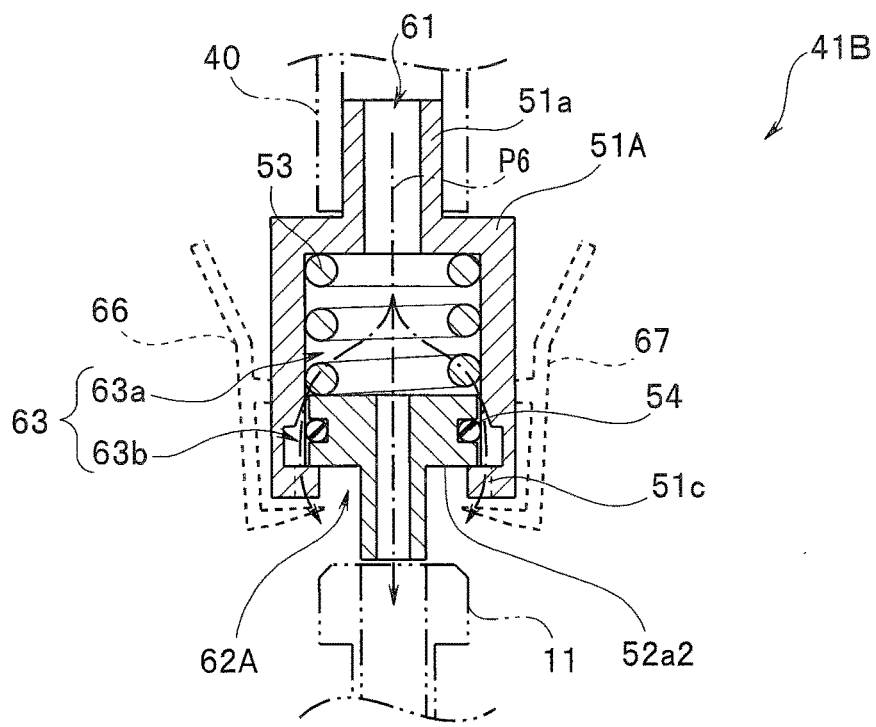
FIG. 13 is a sectional view showing a configuration of a connector 41B of a modification 2 of the embodiment of the present invention.
Figure 14:
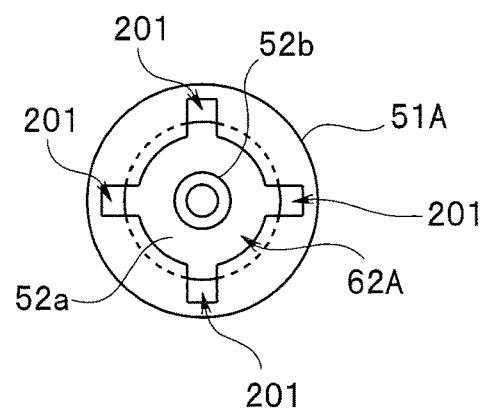
FIG. 14 is a bottom view of the connector 41B according to the modification 2 of the embodiment of the present invention.

FIG. 13 is a sectional view showing a configuration of the connector 41B in the modification 2. FIG. 13 shows a cross section taken along an axial direction of the connector 41B having a substantially cylindrical shape. FIG. 14 is a bottom view of the connector 41B.

As shown in FIG. 14, an outflow port 62A on the distal end side of an outer cylinder member 51A of the connector 41B has a non-circular shape. The connector 41B is configured such that the distal end face 52*a*2 of the advancing/retracting section 52*a* comes into contact with the inward flange section 51*c* of the outer cylinder member 51A and the advancing/retracting section 52*a* is not pushed out to the distal end side of the outer cylinder member 51.

However, the outflow port 62A has a shape forming a plurality of gaps 201 through which the second inner circumferential section 63*b* of the outer cylinder member 51 and an outer side of the outer cylinder member 51 communicate when the distal end face 52*a*2 of the advancing/retracting section 52*a* is in contact with the inward flange section 51*c* of the outer cylinder member 51A.

(Action)

Figure 15:
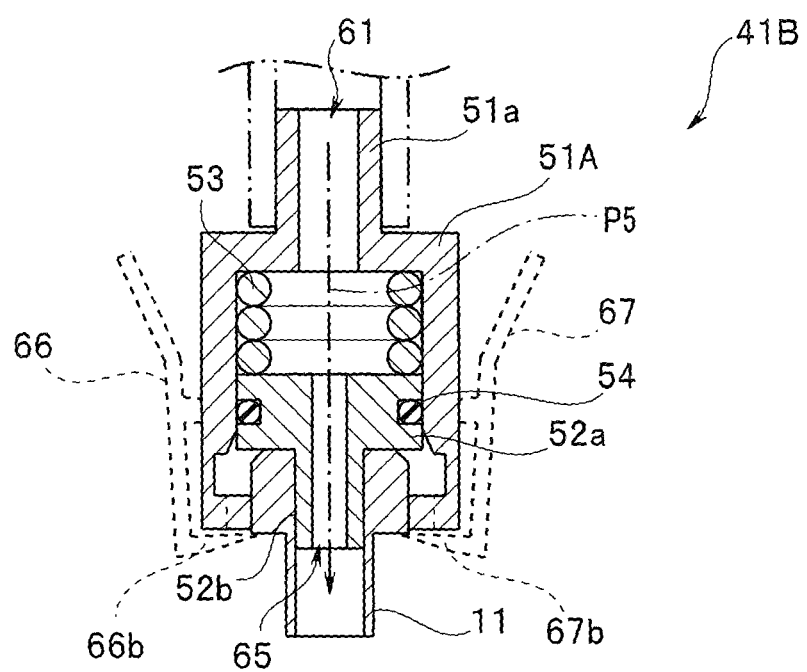
FIG. 15 is a sectional view showing a state in which the connector 41B is correctly attached to the pipe sleeve 11 according to the modification 2 of the embodiment of the present invention.

FIG. 15 is a sectional view showing a state in which the connector 41B is correctly attached to the pipe sleeve 11.

The user inserts the pipe sleeve 11 of the endoscope 2 into the inner side of the inward flange section 51*c* of the outer cylinder member 51A to press the connector 41 against the pipe sleeve 11. Then, the urging member 53 is compressed and the advancing/retracting section 52*a* moves to an inner side of the first inner circumferential section 63*a* of the internal space 63.

The hook sections 66*b* and 67*b* engage with an outward flange section 11*a* of the pipe sleeve 11, whereby the connector 41B is fixed to the pipe sleeve 11.

As shown in FIG. 15, when the connector 41B is correctly fixed to the pipe sleeve 11, liquid such as a cleaning solution supplied through the cleaning tube 40 flows into the inner side of the first inner circumferential section 63*a* from the inflow port 61 of the connector 41B.

The O-shaped ring 54 prevents the liquid from flowing into an inner side of the second inner circumferential section 63*b* from the gap between the advancing/retracting section 52*a* and the inner circumferential surface 51*ba*. Therefore, the liquid is supplied into the pipe sleeve 11 through the through-path 65 formed in the inner cylinder member 52 as indicated by an alternate long and short dash line P5.

Action at the time when the connector 41A is not correctly fixed to the pipe sleeve 11 and is off the pipe sleeve 11 is explained.

When the connector 41A is not correctly fixed to the pipe sleeve 11 and is off the pipe sleeve 11, as shown in FIG. 13, the advancing/retracting section 52*a* is pushed by the urging member 53 and comes into contact with the inward flange section 51*c*.

In this state, the O-shaped ring 54 is not in contact with the inner circumferential surface 51*bb* and a gap is formed between the advancing/retracting section 52*a* and the inner circumferential surface 51*bb*. Further, since the plurality of gaps 201, through which the second inner circumferential section 63*b* of the outer cylinder member 51 and the outer side of the outer cylinder member 51 communicate, are formed, the liquid that flows into the inner side of the first inner circumferential section 63*a* from the inflow port 61 of the connector 41B flows into the second inner circumferential section 63*b* from the gap between the advancing/retracting section 52*a* and the inner circumferential surface 51*bb*. Further, the liquid flows out to an outside of the connector 41B from the gaps 201 as indicated by an alternate long and short dash line P6.

At this point, the liquid flows out from the through-path 65 of the inner cylinder member 52. However, in addition, the liquid flows out from the plurality of gaps 201 as well. Therefore, a flow rate of the liquid supplied through the cleaning tube 40 increases.

In this modification 2, as in the embodiment, a size of the plurality of gaps is designed such that a difference between the flow rate Qa of the liquid flowing inside the cleaning tube 40 when the connector 41B is correctly fixed to the pipe sleeve 11 and the flow rate Qb of the liquid flowing inside the cleaning tube 40 when the connector 41 is off the pipe sleeve 11 is detected by the flow meter provided in the cleaning apparatus 1 as, for example, equal to or larger than 0.005 L/Min.

Therefore, when the connector 41B is not correctly fixed to the pipe sleeve 11 and is off the pipe sleeve 11, since the liquid is fed out from the plurality of gaps 201, which are the through-holes, as well, a change in the flow rate of the liquid flowing inside the cleaning tube 40 can be detected by the flow meter inside the cleaning apparatus 1.

(Modification 3)

In the connector 41 in the embodiment explained above, the watertight section 54 is provided in the advancing/retracting section 52*a*. However, in a modification 3, the watertight section 54 is provided in the first inner circumferential section 63*a* of the outer cylinder member 51 as shown in FIG. 16 and FIG. 17.

Differences of the modification 3 from the embodiment are explained below. However, the other structures and effects are as explained in the embodiment. Therefore, explanation of the structures and the effects is omitted.

Figure 16:
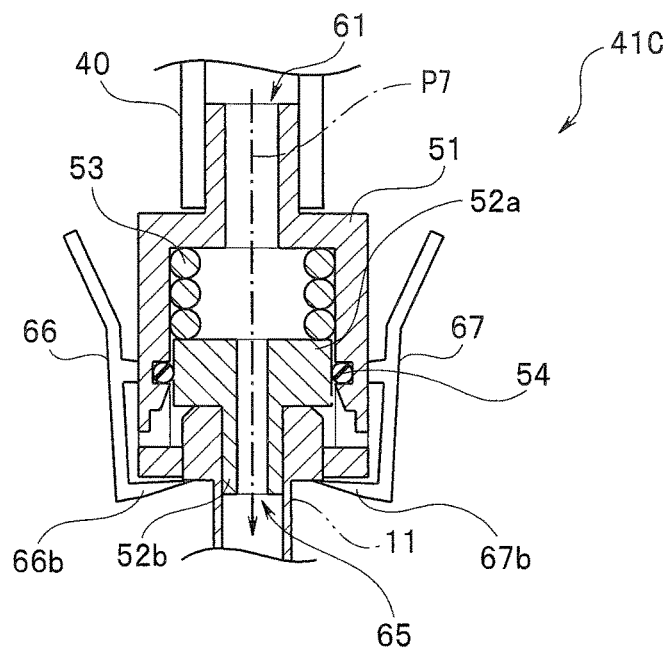
FIG. 16 is a sectional view showing a configuration of a connector 41C at the time when the connector 41C is correctly fixed to the pipe sleeve 11 according to a modification 3 of the embodiment of the present invention.
Figure 17:
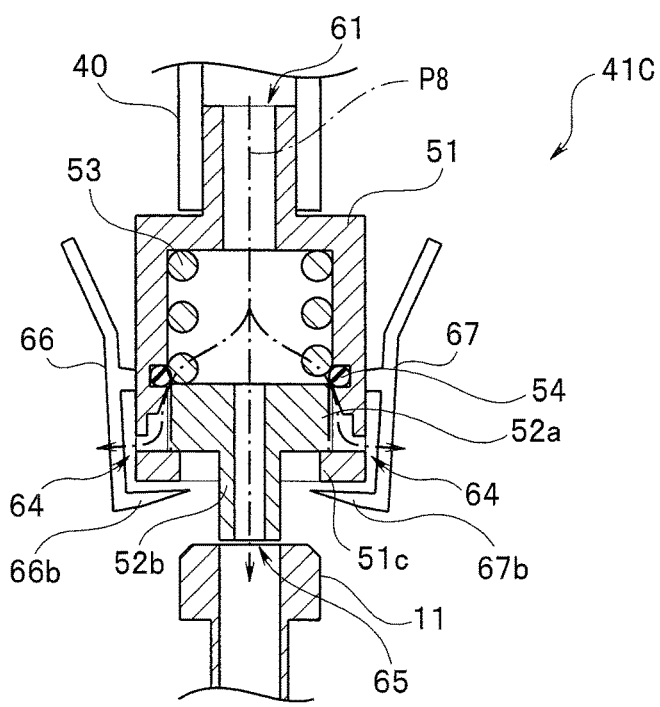
FIG. 17 is a sectional view showing a configuration of the connector 41C at the time when the connector 41C is not correctly fixed to the pipe sleeve 11 and is off the pipe sleeve 11 according to the modification 3 of the embodiment of the present invention.

FIG. 16 is a sectional view showing a configuration of a connector 41C in this modification 3 at the time when the connector 41C is correctly fixed to the pipe sleeve 11.

When the connector 41C is correctly fixed to the pipe sleeve 11, the advancing/retracting section 52*a* is pushed into the first inner circumferential section 63*a* by the pipe sleeve 11 of the endoscope. The advancing/retracting section 52*a* and the first inner circumferential section 63*a* are arranged side by side in a watertight manner sandwiching the watertight section 54. In this case, water tightness is kept between the advancing/retracting section 52*a* and the first inner circumferential section 63*a* by the watertight section 54. Therefore, the fluid that flows in from the inflow port 61 flows out from only the through-path 65 as indicated by an alternate long and short dash line P7.

FIG. 17 is a sectional view showing a configuration of the connector 41C at the time when the connector 41C is not correctly fixed to the pipe sleeve 11 and is off the pipe sleeve 11.

When the connector 41C is not correctly fixed to the pipe sleeve 11, the advancing/retracting section 52a is pushed out by the urging member 53 to a position where the advancing/retracting section 52a comes off the watertight section 54. In this case, since the watertight section 54 for keeping water tightness is absent between the advancing/retracting section 52a and the outer cylinder member 51, a gap into which the fluid enters is formed. Therefore, when the connector 41C is not correctly fixed to the pipe sleeve 11, the fluid flows out from not only the through-path 65 but also from the gap between the inner cylinder member 52 and the outer cylinder member 51 as indicated by an alternate long and short dash line P8.

In the modification 3, as in the embodiment, the second inner circumferential section 63b having the inner diameter larger than the inner diameter of the first inner circumferential section 63a is provided. The fluid flows out passing between the advancing/retracting section 52a and the second inner circumferential section 63b.

(Modification 4)

Figure 18:
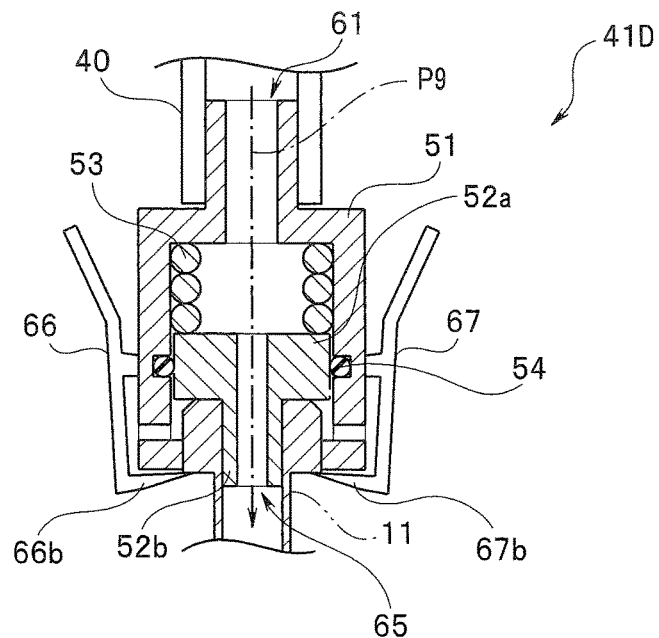
FIG. 18 is a sectional view showing a configuration of a connector 41D at the time when the connector 41D is correctly fixed to the pipe sleeve 11 according to a modification 4 of the embodiment of the present invention.
Figure 19:
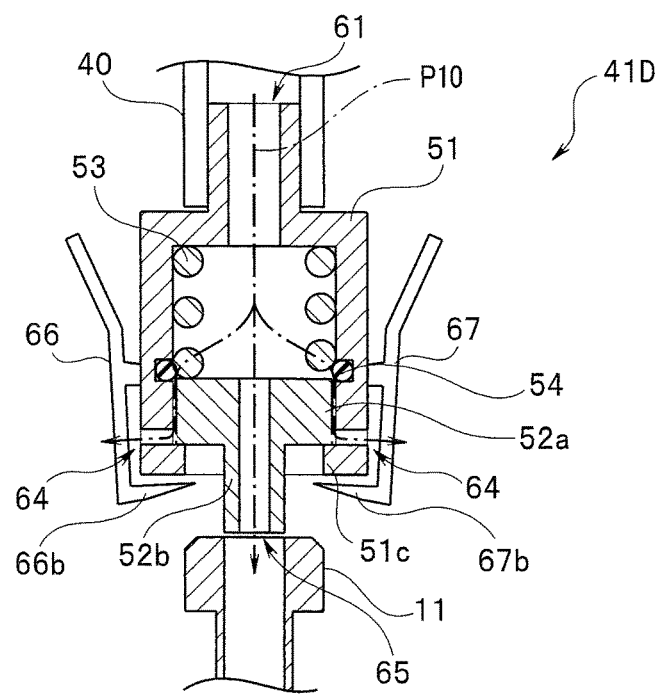
FIG. 19 is a sectional view showing a configuration of the connector 41D at the time when the connector 41D is not correctly fixed to the pipe sleeve 11 and is off the pipe sleeve 11 according to the modification 4 of the embodiment of the present invention.

In the modification 3, the watertight section 54 is provided in the first inner circumferential section 63a of the outer cylinder member 51 and the second inner circumferential section 63b is provided. However, in the outer cylinder member 51 of a connector in a modification 4, as shown in FIG. 18 and FIG. 19, the second inner circumferential section 63b is not provided. The outer cylinder member 51 has a form in which the first inner circumferential section 63a extends.

FIG. 18 is a sectional view showing a configuration of a connector 41D at the time when the connector 41D is correctly fixed to the pipe sleeve 11 according to the modification 4 of the embodiment of the present invention. FIG. 19 is a sectional view showing a configuration of the connector 41D at the time when the connector 41D is not correctly fixed to the pipe sleeve 11 and is off the pipe sleeve 11 according to the modification 4 of the embodiment of the present invention.

In the case of this modification 4, when the connector 41D is correctly fixed to the pipe sleeve 11, water tightness is kept by the watertight section 54 between the advancing/retracting section 52a and the first inner circumferential section 63a. Therefore, the fluid that flows in from the inflow port 61 flows out from only the through-path 65 as indicated by an alternate long and short dash line P9. When the connector 41D is not correctly fixed to the pipe sleeve 11, the fluid flows out passing through between the advancing/retracting section 52a and the extending first inner circumferential section 63a as indicated by an alternate long and short dash line P10 in FIG. 19.

When the through-hole 64 is provided in the modification 4, the through-hole 64 is provided in the extending first inner circumferential section 63a.

As explained above, according to the embodiment and the respective modifications explained above, it is possible to provide an endoscope connector that can clarify a flow rate difference of fluid between a time when the endoscope connector is correctly connected to the pipe sleeve of the endoscope and a time when the endoscope connector comes off the pipe sleeve and an endoscope cleaning/disinfecting apparatus including such an endoscope connector.

The present invention is not limited to the embodiment explained above. Various changes, alterations, and the like are possible in a range in which the gist of the present invention is not changed.

What is claimed is:

1. An endoscope connector connected to a pipe sleeve of an endoscope, the endoscope connector comprising:
    an outer cylinder member including an inflow port to which a fluid delivering apparatus is connected, an outflow port for feeding out fluid that flows in from the inflow port, a channel that connects the inflow port and the outflow port, and a first inner circumferential section provided on an inner side of the channel;
    an inner cylinder member including an advancing/retracting section disposed to be capable of advancing and retracting along the channel and having an outer diameter smaller than an outer diameter of the first inner circumferential section, and a through-path that pierces through the advancing/retracting section along the channel;
    an urging member disposed in the first inner circumferential section and configured to urge the inner cylinder member toward the outflow port; and
    a watertight section disposed in an outer circumference of the advancing/retracting section or in the first inner circumferential section and configured to fill a gap between the advancing/retracting section and the first inner circumferential section when the advancing/retracting section is disposed in the first inner circumferential section, wherein
    the fluid introduced from the inflow port when the advancing/retracting section and the first inner circumferential section are arranged side by side in a watertight manner sandwiching the watertight section is fed out passing through the through-path, and
    the fluid introduced from the inflow port when the watertight section is not sandwiched by the advancing/retracting section and the first inner circumferential section is fed out passing through the through-path and a gap between the inner cylinder member and the outer cylinder member.

2. The endoscope connector according to claim 1, wherein the outer cylinder member is provided further on the outflow port side than the first inner circumferential section in the channel and includes a second inner circumferential section having an inner diameter larger than an inner diameter of the first inner circumferential section.

3. The endoscope connector according to claim 2, wherein the outer cylinder member includes a through-hole formed in the second inner circumferential section and connected to an outer surface of the outer cylinder member from the second inner circumferential section.

4. The endoscope connector according to claim 3, wherein the fluid introduced from the inflow port when the inner cylinder member is present in the second inner circumferential section is fed out from the through-hole passing through the through-path and the gap between the inner cylinder member and the second inner circumferential section.

5. The endoscope connector according to claim 2, wherein the fluid introduced from the inflow port when the inner cylinder member is present in the second inner circumferential section is fed out from the through-path and the gap formed between the inner cylinder member and the outer cylinder member.

6. The endoscope connector according to claim 1, wherein the outer cylinder member includes an engaging section that engages with the pipe sleeve of the endoscope.

7. The endoscope connector according to claim 1, wherein
- the inner cylinder member includes a pipe sleeve insertion section inserted into the pipe sleeve of the endoscope, and
- the through-path is opened at a distal end portion of the pipe sleeve insertion section.

8. An endoscope reprocessor comprising the endoscope connector according to claim 1.

9. The endoscope reprocessor according to claim 8, wherein the fluid is a cleaning solution for cleaning an inside of a conduit connected to a pipe sleeve of the endoscope, a disinfecting solution for disinfecting the inside of the conduit connected to the pipe sleeve of the endoscope, a sterilizing solution for sterilizing the inside of the conduit connected to the pipe sleeve of the endoscope, or a rinsing solution for rinsing the inside of the conduit connected to the pipe sleeve of the endoscope.

\* \* \* \* \*